United States Patent [19]

Meriläinen

[11] Patent Number: 5,542,414
[45] Date of Patent: Aug. 6, 1996

[54] GAS SUPPLYING HEAD ENCLOSURE WITH EXPANDABLE PRESSURE INDICATOR

[75] Inventor: Pekka Meriläinen, Helsinki, Finland

[73] Assignee: Instrumentarium Corp., Finland

[21] Appl. No.: 114,673

[22] Filed: Aug. 31, 1993

[30] Foreign Application Priority Data

Sep. 3, 1992 [FI] Finland ................................ 923953

[51] Int. Cl.$^6$ .................. A61M 16/00; A62B 18/10; F16K 31/02; A61G 10/00
[52] U.S. Cl. .................. 128/204.22; 128/201.23; 128/201.28; 128/205.26; 128/204.23; 600/21
[58] Field of Search .................. 128/204.21, 204.23, 128/205.26, 202.12, 202.22, 200.24, 201.28, 204.28, 205.23, 204.22, 201.23; 600/21

[56] References Cited

U.S. PATENT DOCUMENTS

| 3,786,809 | 1/1974 | Kitrilakis | 128/205.26 |
|---|---|---|---|
| 3,898,987 | 8/1975 | Elam | 128/205.23 |
| 4,671,297 | 6/1987 | Schulze, Jr. | 128/204.23 |
| 4,763,664 | 8/1988 | Meriläinen | 128/201.23 |
| 4,827,964 | 5/1989 | Guido et al. | 128/204.21 |
| 4,832,042 | 5/1989 | Poppendiek et al. | 128/205.26 |
| 4,856,531 | 8/1989 | Meriläinen | 128/719 |
| 5,335,653 | 8/1994 | Blomqvist | 128/200.24 |

*Primary Examiner*—Kimberly L. Asher
*Attorney, Agent, or Firm*—Andrus, Sceales, Starke & Sawall

[57] ABSTRACT

An apparatus for monitoring a respiratory gas flow, comprising a gas collector unit (8), which separates an ambient gas space from that remaining inside the gas collector unit and in which a patient respires the gas contained in said gas collector unit. A conduit (7) flows a respiratory gas from one or more gas sources (1) into the gas collector unit (8) to be respired by a patient, and a conduit (14) delivers a respiratory gas, which at least partially contains a gas exhaled by a patient, from the gas collector unit (8) to a measuring device (13) for examination. The pressure difference between a gas space protected by the gas collected unit and a gas space existing outside it is indicated by a pressure-difference detecting element (17). A method for monitoring a respiratory gas flow compares the pressure of a respiratory gas existing inside the gas collector unit (8) with that prevailing outside the gas collector unit and adjust gas flows accordingly.

12 Claims, 2 Drawing Sheets

GAS SUPPLYING HEAD ENCLOSURE WITH EXPANDABLE PRESSURE INDICATOR

BACKGROUND OF THE INVENTION—FIELD OF THE INVENTION

The present invention relates to an apparatus suitable for monitoring a respiratory gas flow, comprising a gas collector unit, which separates an ambient gas space from that remaining inside the gas collector unit, a patient respiring a gas contained in said gas collector unit, a conduit for flowing a respiratory gas from one or more gas sources into the gas collector unit to be respired by a patient, and a conduit for delivering a respiratory gas, which at least partially contains a gas exhaled by a patient, from the gas collector unit to a measuring device for examination. The invention relates also to a method suitable for monitoring a respiratory gas flow.

BACKGROUND OF THE INVENTION—DESCRIPTION OF THE RELATED ART

Human metabolism can be measured by means of so-called indirect calorimetry, wherein the concentrations and flow rates of respiratory or airway gases are measured for the determination of oxygen consumption (VO2) and carbon dioxide output (VCO2). The measuring results can be used for calculating an estimate for energy consumption and respiratory quotient (RQ=VCO2/VO2) as well as for the amount of carbohydrates and fats consumed by an organism. The burning of carbohydrates produces carbon dioxide in an amount equal to the consumption of oxygen, whereby RQ=1, while the burning of fats gives a corresponding ratio of approximately 0,7.

Indirect calorimetry is particularly used for assessing the nutritive need of critically ill patients fed intravenously, i.e. parenterally or with the help of a gastric tube, i.e. enterally in the intensive care units of hospitals. Since a large number of these patients are in a respirator, the mixing of inspiratory gases and the collection of expiratory gases for measurement directly from the respiratory cycle of a patient is relatively simple. One apparatus intended for measuring patients connected to a respirator is described in U.S. Pat. No. 4,856,531.

The need for applying indirect calorimetry also to spontaneously breathing patients has increased continuously. This concerns e.g. patients suffering from cancer and various metabolic diseases. One gas collector unit intended for the metabolic measurements of spontaneously breathing patients is described in U.S. Pat. No. 4,763,664. A gas collector unit is often called a canopy.

During or after various medical procedures, the critically ill, spontaneously breathing patients are supplied with extra oxygen, whenever necessary. There are solid arguments for performing metabolic measurements also on such adult and child patients who are primarily suffering from cardiac and pulmonary impediments. The problems of currently available gas collector units, like the one mentioned above, become evident when it is time to supply a patient with air that contains more oxygen than ambient air. Thus, the gas collector unit should be absolutely tight. When a gas collector unit is used for breathing air having the same oxygen content as ambient air, a minor leak is not critical but, whenever the oxygen content of a gas collector unit differs from that of ambient air, even a minor leak may produce a major measuring error distorting e.g. the value of energy consumption or respiratory quotient.

U.S. Pat. No. 5,335,653 discloses a method and apparatus capable of resolving the basic problems relating to gas collector unit measuring effected by means of oxygen-enriched air. The cited application discloses gas collector unit embodiments based on the use of both a double and a single wall. In principle, the double-walled gas collector unit does not require as complete a sealing around the head of a patient as a single gas collector unit. On the other hand, the single gas collector unit is easier to manufacture and also beneficial in view of keeping it clean. The double or dual gas collector unit solution is also inconvenient to use because of its large size.

SUMMARY OF THE INVENTION

An object of this invention is to eliminate the above problems. An object is to provide a method and apparatus for monitoring a respiratory gas flow in view of maintaining the pressure in a gas collector unit at a desired level as a patient respires a gas contained in the gas collector unit. Another object is to provide a method and apparatus for monitoring a respiratory gas flow, such that the content of some respiratory component gas, such as e.g. oxygen, delivered into a gas collector unit, would remain stable. A particular object is to provide a method and apparatus capable of preventing a detrimental gas leak occurring into a gas collector unit from outside. An object is also to provide a method and apparatus capable of preventing or at least nullifying the significance of a detrimental gas leak occurring from a gas collector unit to environment. A further object is to provide a method and apparatus, whereby a gas containing more oxygen than the air surrounding a patient can be delivered to a patient by way of a simple gas collector unit while avoiding metabolic measuring errors. Yet another object is to provide a method and apparatus for monitoring the respiration of a patient breathing a gas contained in a gas collector unit. The characterizing features of a method and apparatus of the invention are set forth in the annexed claims.

The invention is based on comparing the pressure of a respiratory gas contained in a gas collector unit with the pressure prevailing outside the gas collector unit. Thereafter, the internal respiratory gas pressure of a gas collector unit can be adjusted to a desired level, if necessary. This is usually effected at the time a patient has been brought to breathe a gas in a gas collector unit. In most cases, a gas collector unit is positioned around the head of a patient and sealed on his or her neck, whereby the gas flows into or out of a gas collector unit are as negligible as possible. The internal pressure of a gas collector unit is adjusted to be at least equal to the external pressure or usually the prevailing ambient pressure. In practice, the internal pressure of a gas collector unit should preferably be higher than the pressure prevailing outside it. In order not to produce too much of a leak from a gas collector unit outwards, the pressure prevailing inside a gas collector unit should preferably be less than 1 mmH2O, but even more preferably less than 0,1 mmH2O higher than that prevailing on the outside. It is often sufficient that the pressure of a gas collector unit be set at a desired level at the beginning of a measuring process, whereby the pressure of a gas collector unit need not be necessarily changed afterwards any more. However, monitoring should be continued throughout a measuring process to confirm that the pressure of a gas collector unit is appropriate.

The respiratory gas pressure of a gas collector unit is regulated by means of a flow rate delivered therein. Into a gas collector unit is typically supplied or delivered at least air and, if necessary, oxygen whenever a patient should receive a respiratory gas richer in oxygen than normal air whereby, if the components or concentrations thereof contained in a gas are different from the situation prevailing outside, the respiratory gas pressure of a gas collector unit must be brought to a desired level. The regulation of a flow rate is effected by means of a flow regulating element. Prior to the combination of two or more gas flows together, the flow regulating elements are used to adjust each flow to a desired level. Mixing the flows together is preferably effected e.g. by means of a pneumatic element, such as an ejector, having its operation based on the use of a pressure gas. In the case of one preferred embodiment of the invention, the operation of an ejector is based on pressurized oxygen for mixing oxygen and air together.

The flow rate towards a gas collector unit must exceed that delivered to a measuring device, such as that delivered from a gas collector unit e.g. to a metabolic monitor. The extra flow is passed by a gas collector unit e.g. into room air. This can be effected simply by tapping a gas conduit extending between an oxygen gas source and a gas collector unit, such that one branch leads into room air while the other branch extends to a gas collector unit. The by-pass flow can be used for maintaining the stable contents of air and oxygen for obtaining a uniform mixing of oxygen into the air flow. Thus, the pressure fluctuations caused in a gas collector unit by the inspiration and expiration of a patient are not able to affect the progress of a flow advancing towards a gas collector unit, which flow would otherwise be alternately rapid and alternately nearly stagnant leading to a fluctuation in the oxygen content of a gas arriving in a gas collector unit.

The invention is based on detecting a difference between the pressure prevailing inside a gas collector unit and that prevailing on the outside thereof. This purpose is preferably served by a pressure-difference detecting element capable of comparing the pressure prevailing inside a gas collector unit with that prevailing on the outside thereof. The reason for this is that the relevant pressure differences between a gas collector unit and ambient air are very small, which requires a high accuracy of measurement. One preferred pressure-difference detecting element is such that the position of some portion of said element changes as the pressure switches in a gas collector unit from positive to negative pressure or vice versa to make visual observation hopefully possible. Usually this type of element is deformable, such as e.g. a diaphragm which is highly responsive. A change of size is also easy to observe. The diaphragm is preferably made of a gas impermeable material, e.g. a metallized foil having typically a thickness of 10 micrometers. The diaphragm thickness should preferably be less than 100 µm, but most preferably less than 50 µm. The diaphragm is installed between the gas space of a gas collector unit and ambient air, the pressure of a gas collector unit prevailing on one side and that of ambient air on the other side thereof. Bulging of the diaphragm in either or at least in one direction indicates that either a positive or a negative pressure prevails inside a gas collector unit. The degree of bulging can be used for determining the pressure prevailing or existing inside a canopy. The accurate quantitative result is not necessarily obtainable or even required, but a positive or a negative pressure prevailing in a gas collector unit is very accurately indicated by such element. Thus, the most important point is to know that a positive pressure, preferably as low as possible, is prevailing inside a gas collector unit, whereby a possible leak from a gas collector unit is directed outwards and the measuring error remains equally small for both carbon dioxide and oxygen.

According to the invention, the pressure-difference detecting element further serves as an indicator for the respiration of a patient. Said element comprises a diaphragm which moves reciprocally in time to respiration, bulging outwards during the expiration of a patient and urging towards a reverse movement during the expiration of a patient. In time to respiration the volume of a gas collector unit changes with the diaphragm moving either out- or inwards. This change of volume is also useful as an equalizer of the flow fluctuation occurring in time to respiration.

Thus, this invention facilitates the supply of a gas with a stable oxygen content into a gas collector unit while effecting the regulation of the internal pressure of a gas collector unit.

BRIEF DESCRIPTION OF THE DRAWING

The invention will now be described in more detail with reference made to the accompanying drawings, in which.

DESCRIPTION OF THE PREFERRED EMBODIMENT

Figure 1:
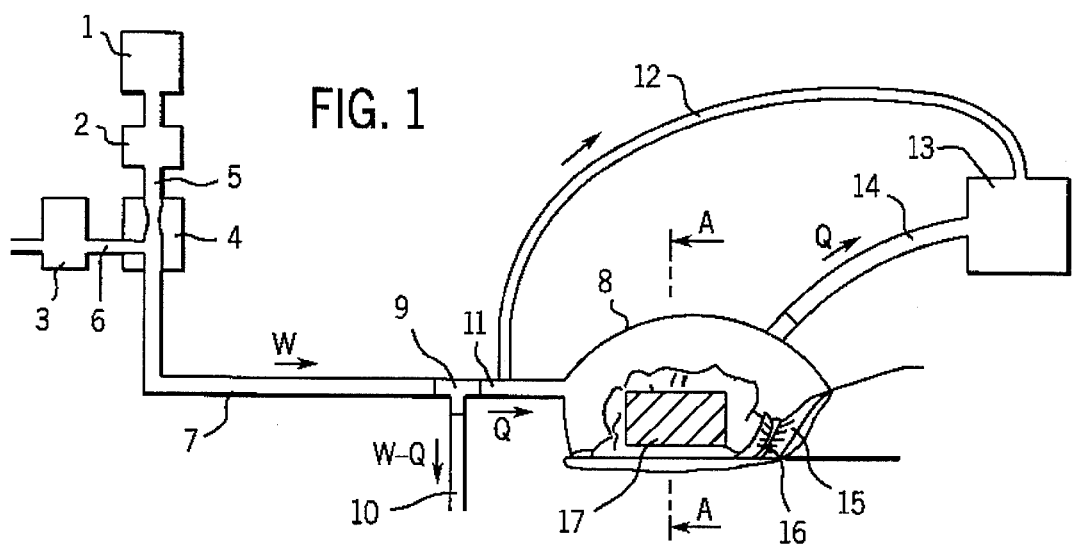
FIG. 1 shows a schematic general view of an assembly of the invention for metabolic measurements on patients respiring a gas containing more oxygen than ambient air.

A gas source 1 shown in FIG. 1 contains oxygen in this exemplary embodiment and a gas delivered therefrom is mixed with another gas, which in this case is air. The air can be obtained directly from the space a patient is located in, i.e. often from the same room which thus serves also as a gas source. Adjustment of the total flow and mixing ratio of oxygen and air for a patient is effected by means of flow regulating elements 2 and 3, which are preferably needle valves. However, the operation of common commercially available valves proceeds without any scale that could simplify the regulation of gas flows. These two flows are delivered to a patient preferably by way of a pneumatic element 4, the mixing of gases together occurring therein. An example of such pneumatic element is an ejector receiving its driving force from gas source 1. An oxygen jet coming along a conduit 5 from the gas source produces inside the pneumatic element a negative pressure, whereby room air is vacuumed from a conduit 6 to mix with the oxygen gas. The gas mixture flows along a conduit 7 towards a gas collector unit 8, the head of a patient being visible thereinside.

Upstream of the gas collector unit, some of the flow coming from flow regulating elements 2 and 3 is preferably passed by the gas collector unit. In view of passing the gas flow both into and by the gas collector unit, the figure shows a branch-T 9, having a conduit 10 coupled therewith for a by-pass flow. The volume of this conduit 10 is preferably at least equal to the single respiratory volume of a patient, whereby no undesired gas is able to penetrate into the gas collector unit along conduit 10 at the time the respiratory direction of a patient reverses. More preferably, the volume of conduit 10 is larger than the maximum single volume of respiration. In practice, the single volume is often in the order of 0,5–1 liters.

From the branch-T to gas collector unit 8 extends a conduit 11. Preferably, a minor portion of the flow coming from flow regulating elements 2 and 3 is delivered along conduit 10 past the gas collector unit and, thus, a major portion of the flow is carried along conduit 11 to the gas collector unit. A sample of the oxygen content of a gas progressing to the gas collector unit is delivered along a conduit 12 to a measuring device 13. A gas desired from the gas collector unit for examination is preferably also delivered to the same measuring device 13 along a conduit 14. Thus, the measuring device is preferably capable of examining not only the oxygen content but also the carbon dioxide content of a gas. The measuring device can be for example an apparatus described in U.S. Pat. No. 4,856,531, manufactured by Datex-group, Instrumentarium Oy, under the tradename Deltatrac.

The gas collector unit 8 is preferably self-supporting and possibly made of a transparent plastic and fitted with a skirt 15 of a flexible material for facilitating its sealing against the skin of a patient. The sealing is usually provided around the neck of a patient but just as well the sealing could be provided in the area of shoulders or abdomen. The skirt preferably extends underneath the head of a patient as a patient is lying in bed on his or her back. This type of gas collector unit is easy to fit around the head of a patient. The sealing between the neck of a patient and the skirt is further assured in FIG. 1 by means of a sealing member 16, e.g. a velcro type of adhesive tape wrapped around the neck of a patient.

The gas collector unit 8 is provided with a pressure-difference detecting element 17 for observing a pressure difference prevailing between gas collector unit 8 and its surroundings. This particular element 17 is in flow communication both with a gas space inside the gas collector unit, which gas a patient is breathing, and with a gas space outside the gas collector unit that the prevailing internal pressure is to be compared with. Therefore, such element is preferably mounted on a side of the gas collector unit. The number of pressure-difference detecting elements can be one or more.

Figure 2:
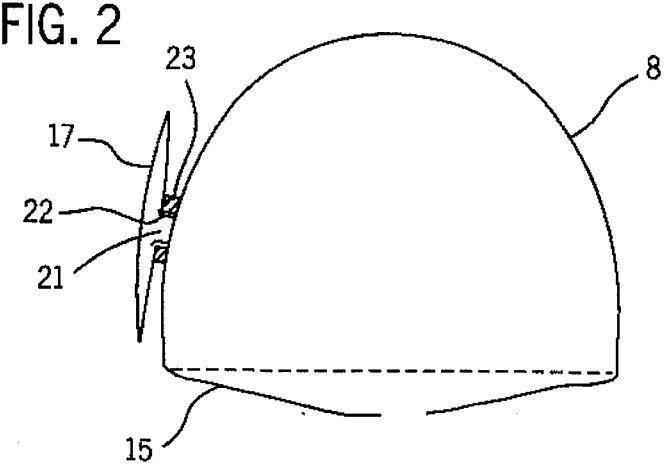
FIG. 2 shows a cross-section of the gas collector unit shown in FIG. 1 along a line A—A.
Figure 3:
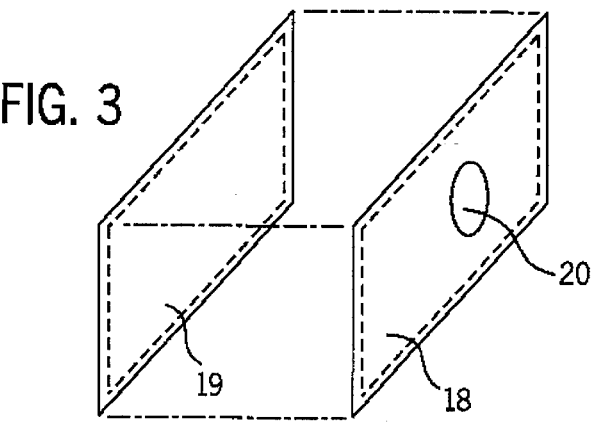
FIG. 3 is a more detailed view of the components included in a pressure-difference detecting element according to a preferred embodiment of the invention coupled with a gas collector unit.

FIG. 1 and especially FIG. 2 illustrates a preferred solution for a pressure-difference detecting element 17. It comprises a diaphragm, which is preferably made of a metallized foil and is positioned between the interior and exterior of a gas collector unit. On the other hand, FIG. 3 illustrates in more detail the configuration of one preferred pressure-difference detecting element made of a diaphragm. It comprises two pieces of diaphragm 18 and 19, whose appropriate size in this case is 10×20 cm. These pieces can be hot sealed by the edges thereof against each other hermetically to form a pouch. Alternatively, the pouch could be constructed even from a single piece of diaphragm by folding the diaphragm to form two opposite walls, whose edges are then sealed hermetically with a clear gas space remaining between the opposite walls.

One piece 18 of diaphragm is provided with a hole 20 whereby the gas space developed and remaining between the walls of a diaphragm is in flow communication with the gas space of a gas collector unit. Said pressure-difference detecting element is secured to an edge 22 of a port 21 made in the side of a gas collector unit e.g. as shown in FIG. 2, the port 21 of a gas collector unit being aligned with the corresponding hole 20 included in the pressure-difference detecting element. In FIG. 2, in view of preventing leaks, said pouch-like pressure-difference detecting element 17 is secured to gas collector unit 8 by using a fastening means 23, preferably made of two-sided annular adhesive tape. Said port 21 in the side of a gas collector unit can for example have a diameter of 1–2 cm, when the pouch consists of diaphragm pieces having a size of 10×20 cm. The size of a port depends on the size of a pouch. In a preferred case, said port 21 is about 10% of the size of a pouch. The hole 20 of pressure-difference detecting element 17 is also in the same order as the port 21 of a gas collector unit.

This type of pressure-difference detecting element made of diaphragm is so inexpensive that merely for reasons of hygiene it pays to replace it with a new one for each individual patient. In addition to what is mentioned above, the material for a pouch used as a pressure-difference element can be any sufficiently thin and sufficiently gastight diaphragm provided, however, that the inner walls of a pouch do not adhere readily to each other.

Figure 4A:
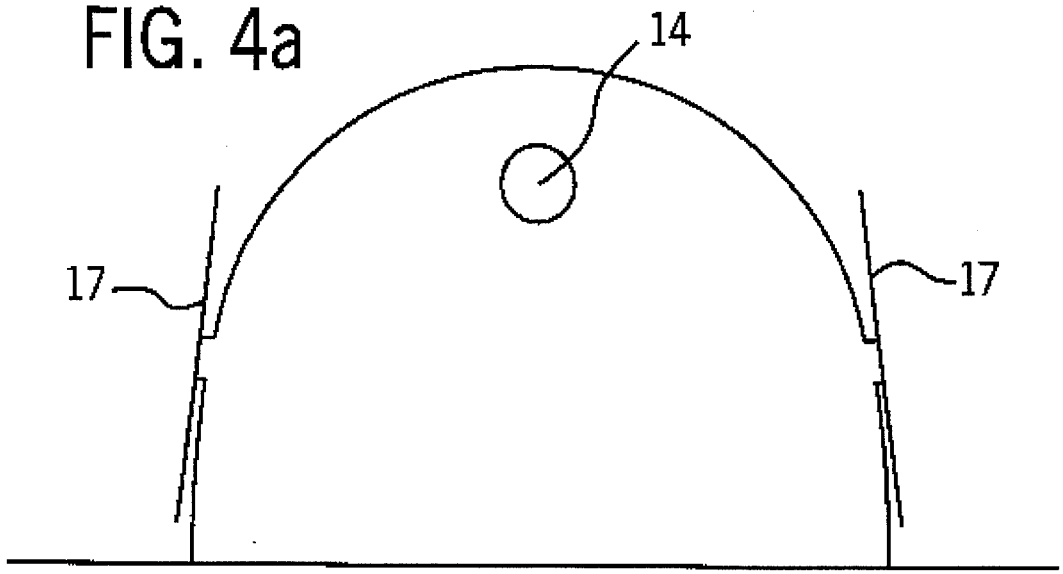
FIG. 4a and 4b illustrate typical positions in various pressure situations assumed by a pressure-difference detecting element associated with a gas collector unit.
Figure 4B:
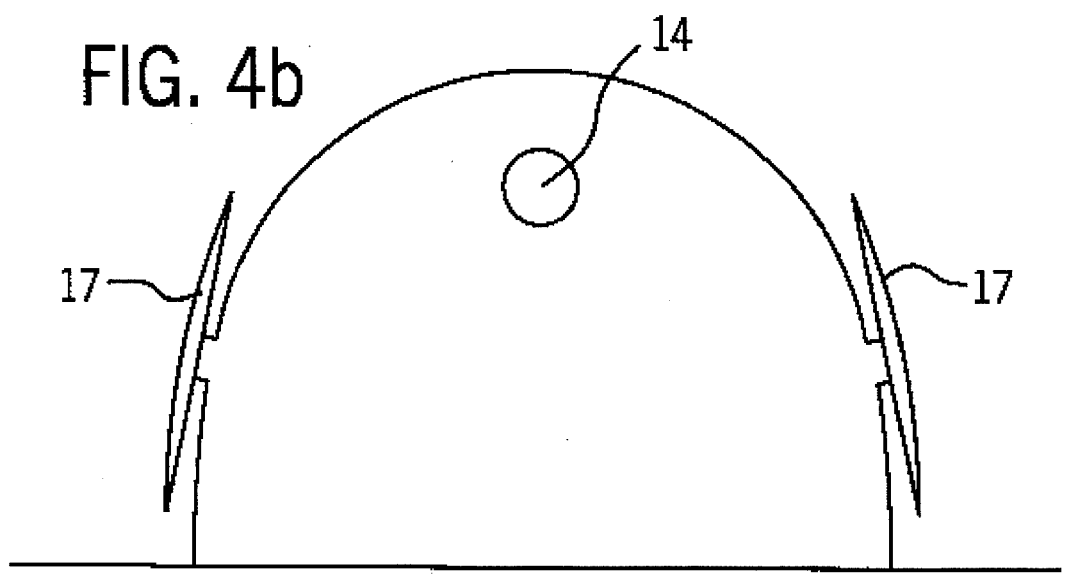

FIGS. 4a and 4b illustrate the behaviour of pressure-difference detecting elements, in this case two elements, coupled with a gas collector unit, when there is a negative pressure (4a) and a positive pressure (4b) inside a gas collector unit in relation to external pressure. Hence, the behaviour of a pouch-like pressure-difference detecting element reveals the state for visually determining a pressure condition which is preferred in terms of measuring accuracy. As the pouch is pressing tightly against the surface of a gas collector unit, as shown in FIG. 4a, such that it is possibly sucked into a concave form within the area of port 21, a negative pressure is indicated and, respectively, as the pouch is even slightly bulged off said port 21, as shown in FIG. 4b, a positive pressure is indicated. In a typical case, the pouch may bulge about 5 mm outwards through the action of a positive pressure existing in a gas collector unit. The pouch normally performs a reciprocating action at the rate of respiration, the size thereof growing during expiration and diminishing during inspiration. The pressure of a gas collector unit is adjusted by means of flow regulating elements 2 and 3, such that, during an inspiration cycle, the pressure drops momentarily to a level as close to zero pressure as possible. The pressure level inside a gas collector unit depends on the flow resistance of branch-T 9 located upstream of a gas collector unit and on the flow rate. The movement of a pouch is a clear indication to the operator that the patient is breathing and the movement can also be used for calculating the respiration frequency. This is an important safety aspect when measuring seriously ill patients. It is true that a measuring device 13 is capable of concluding the stoppage of or a long pause in respiration also from gas readings, but this occurs more slowly, typically as much as 30 seconds later. However, the bulging volume of a pouch does not directly indicate the single respiratory volume of a patient, as the inner volume of a gas collector unit is altered in any case according to respiration by a flexible skirt placed around the neck of a patient.

As arguments for the significance of the invention, the following calculation is presented to indicate the effect that a minor leak from a gas collector unit outwards during the state of a positive pressure has upon the results if compared to an inward leak during the state of a negative pressure. Presuming that the flow of rate is 40 l/min through a gas collector unit and the leakage is 1% thereof or 0.4 l/min. Presuming that the carbon dioxide output and oxygen consumption of a patient are both 200 ml/min. Thus, the average diluted gas content differences are 0.5% for both oxygen and carbon dioxide. If the presumed oxygen level is 40%, the air flow of 0.4 l/min leaking in at the time of a negative pressure and containing 21% of oxygen dilutes the expiratory oxygen content to be measured by 40–(0.4*21+39.6*40)/40=0.2%. Thus, the oxygen difference obtained as a measuring result changes from 0.5% to 0.7%, which is a 40% proportional error. The mathematical pattern of oxygen consumption amplifies the error in oxygen difference at high oxygen levels and it can be calculated that the resulting oxygen consumption is then as much as 67% too high. On the other hand, the inward leak of air does not cause any error at all in carbon dioxide output. The outward leak means that expiratory gases are escaping from a gas collector unit. If the outward leak is said 1% or 0.4 l/min, it can be calculated that the carbon dioxide output is 1% and oxygen consumption 1.6% too low. Hence, it can be concluded that, in view of the accuracy of measurement of oxygen consumption, it is absolutely crucial that the leak be directed outwards. Despite this, the leak must of course be as negligible as possible.

The invention offers an improved possibility for controlled regulation of a pressure condition prevailing within a gas collector unit over a dual gas collector unit assembly disclosed in the Patent application FI 911807. In reference to FIG. 1, a simple calculation can be presented for the pressure prevailing within a gas collector unit. Supposing that the flow vacuumed by a measuring device through a gas collector unit is Q and the flow produced by an ejector is W. In this case, the flow passing by a gas collector unit is W–Q. Supposing that the flow resistance in conduit 11 between branch-T 9 and a gas collector unit is R7 and the flow resistance in conduit 10 extending from branch-T 9 past gas collector unit 8 is R6. The, the crossing point of branch-T 9 contains a positive pressure of (W–Q)*R6 over the surroundings. The pressure drop from the crossing point into the gas collector unit is in turn Q*R7. Thus, the pressure inside the gas collector unit in relation to the surroundings is (W–Q)*R6–Q*R7. Flow resistance R6 can be maintained stable and selected such that the positive pressure limit within a gas collector unit is typically exceeded by the value of W, which is about 1.5 times the gas collector unit flow Q. Thus, the adjustment of flow W in a given situation can be effected directly by monitoring the positive pressure limit indicated by pouch-like pressure detecting element 17 without having to know exact values for either of flows W and Q. This is particularly beneficial in the case of an ejector type pneumatic element 4, which dispenses highly stable oxygen dosage but does not have an accurate quantitative flow control.

The above calculation also illustrates the control-related practical difficulties in the case of a dual gas collector unit. Even if the inner gas collector unit were provided with a pressure pouch of this invention, the possibilities of controlling the internal pressure thereof would be poor since the equivalent of stable resistance R6 therein is an indefinite and varying flow resistance depending on a leakage allowed by the outer canopy skirt.

The invention is by no means limited to the above embodiments but various details of the invention can be modified within the scope of the annexed claims. A pressure detecting element described in the invention can also be used merely as a detector of the respiration of a patient e.g. in an old type of canopy, as described in U.S. Pat. No. 4,763,664.

I claim:

1. An apparatus providing gas from a gas source to a patient for respiration by the patient comprising:

a supply conduit (7) connectable to the gas source;

a gas collector unit (8) having an interior for receiving the head of the patient and in which the patient respires gas contained in the interior of the gas collector unit, said gas collector unit separating the interior of said unit from the ambient atmosphere for the apparatus, said gas collector unit having an inlet connected to said supply conduit;

discharge conduit means (14) coupled to said gas collector unit for discharging gas expired by the patient; and pressure difference indicating means (17) for indicating a pressure difference between the pressure in the interior of said gas collector unit and the pressure of the ambient atmosphere, said pressure difference indicating means being coupled to said gas collector unit and having an element subjected to the pressure in the interior of said gas collector unit and to the ambient atmosphere pressure, said element undergoing a change in physical dimension responsive to a difference in the interior and ambient atmosphere pressures, said element being directly observable so that the dimensional condition of said element comprises the indication of the pressure difference, said pressure difference indicating means (17) comprising at least one flexible wall member formed to have a pair of opposing walls with a hermetically sealed space therebetween, one of said walls having an opening which is in fluid communication with a port in said gas collection unit.

2. An apparatus as set forth in claim 1, characterized in that said at least one flexible wall member comprises a diaphragm formed of said pair of opposing walls, said pair of opposing walls being flexible and hermetically sealed together along their edges, one of said walls having said opening which is in fluid communication with said port in said gas collection unit.

3. An apparatus as set forth in claim 2, characterized in that the diaphragm is made of a foil material.

4. An apparatus as set forth in claim 1, characterized in that said gas source comprises a plurality of gas sources and wherein said supply conduit includes a gas powered means for mixing the gases upstream of the collector unit.

5. An apparatus as set forth in claim 1, further including at least one flow regulating element suitable for regulating gas flow to the gas collector unit responsive to the observed condition of said pressure difference indicating means.

6. An apparatus as set forth in claim 1, wherein said supply conduit (7) includes means for branching off a portion of the gas from the gas source upstream of said gas collector unit.

7. An apparatus as set forth in claim 6 wherein said branching off means includes a stable flow resistance means for establishing the pressure in said gas collector unit by controlling the flow rates of gas to and from said gas collector unit.

8. The apparatus as set forth in claim 1 further comprising a detector for the respiration of a patient.

9. The apparatus as set forth in claim 1 wherein said supply conduit (7) supplies a gas having an enriched oxygen content as compared to normal air.

10. An apparatus as set forth in claim 1, characterized in that the at least one wall member is made of a foil material.

11. An apparatus as set forth in claim 1 characterized in that said pressure difference indicating means is mounted directly on said gas collection unit.

12. An apparatus as set forth in claim 1 characterized in that the pressure difference indicating means is formed to indicate whether the interior pressure is positive or negative with respect to the ambient atmosphere pressure.

\* \* \* \* \*